(12) United States Patent
Chan et al.

(10) Patent No.: US 11,963,942 B2
(45) Date of Patent: *Apr. 23, 2024

(54) ORAL TAXANE COMPOSITIONS AND METHODS

(71) Applicant: Athenex HK Innovative Limited, Hong Kong (CN)

(72) Inventors: Denise S. B. Chan, Hong Kong (CN); Ming Tsung Lee, Hong Kong (CN); Weng Li Yoon, Hong Kong (CN); Johnson Yiu-Nam Lau, Newport Beach, CA (US)

(73) Assignee: Health Hope Pharma Ltd, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 17/069,557

(22) Filed: Oct. 13, 2020

(65) Prior Publication Data

US 2021/0023042 A1 Jan. 28, 2021

Related U.S. Application Data

(63) Continuation of application No. 15/277,890, filed on Sep. 27, 2016, now Pat. No. 10,835,511.

(Continued)

(51) Int. Cl.
*A61K 31/337* (2006.01)
*A61K 9/00* (2006.01)
(Continued)

(52) U.S. Cl.
CPC .......... *A61K 31/337* (2013.01); *A61K 9/0053* (2013.01); *A61K 9/1075* (2013.01);
(Continued)

(58) Field of Classification Search
CPC ..... A61K 31/337; A61K 9/0053; A61K 47/26
See application file for complete search history.

(56) References Cited

U.S. PATENT DOCUMENTS

| 6,469,022 B1 * | 10/2002 | Schellens | A61K 31/47 |
| | | | 514/297 |
| 10,835,511 B2 * | 11/2020 | Chan | A61K 47/14 |

(Continued)

FOREIGN PATENT DOCUMENTS

| CN | 1361677 | 7/2002 |
| CN | 1606437 | 4/2005 |

(Continued)

OTHER PUBLICATIONS

Rege et al. Effects of nonionic surfactants on membrane transporters in Caco-2 cell monolayers, European Journal of Pharmaceutical Sciences, vol. 16, Issues 4-5, 2002, pp. 237-246. (Year: 2002).*

(Continued)

*Primary Examiner* — Carlos A Azpuru
*Assistant Examiner* — Casey S Hagopian
(74) *Attorney, Agent, or Firm* — Fish IP Law, LLP

(57) ABSTRACT

A pharmaceutical composition comprises a taxane (e.g., paclitaxel, docetaxel, cabazitaxel, larotaxel, ortataxel, and/or tesetaxel) in a mixture of first and second surfactants. The absorption of the taxane is increased from the pharmaceutical composition is greater than the sum of the absorption of docetaxel from either the first or the second surfactant. The increase in absorption is especially enhanced when the ratio of the first surfactant to the second surfactant in the pharmaceutical composition is between 60:40 and 85:15 by weight, and the total surfactant weight does not exceed 98% of the total weight. Polysorbate 80, polysorbate 20, and caprylocaproyl polyoxylglycerides serve as suitable first surfactants, and polysorbate 80 or polyethyoxylated castor oil serve as suitable second surfactants. The stability of the (Continued)

pharmaceutical composition may be enhanced by further including a stabilizer (e.g., citric acid and/or ascorbic acid).

15 Claims, 12 Drawing Sheets

Related U.S. Application Data

(60) Provisional application No. 62/234,868, filed on Sep. 30, 2015.

(51) Int. Cl.
  *A61K 9/107* (2006.01)
  *A61K 9/48* (2006.01)
  *A61K 31/4725* (2006.01)
  *A61K 45/06* (2006.01)
  *A61K 47/12* (2006.01)
  *A61K 47/14* (2017.01)
  *A61K 47/26* (2006.01)
  *A61K 47/44* (2017.01)

(52) U.S. Cl.
  CPC ........ *A61K 9/4858* (2013.01); *A61K 31/4725* (2013.01); *A61K 45/06* (2013.01); *A61K 47/12* (2013.01); *A61K 47/14* (2013.01); *A61K 47/26* (2013.01); *A61K 47/44* (2013.01)

(56) References Cited

U.S. PATENT DOCUMENTS

| | | | |
|---|---|---|---|
| 2004/0092428 A1* | 5/2004 | Chen | A61K 9/1075 |
| | | | 424/452 |
| 2005/0025792 A1* | 2/2005 | Peracchia | A61K 9/1075 |
| | | | 424/400 |
| 2005/0158389 A1 | 7/2005 | Domb | |
| 2017/0087121 A1* | 3/2017 | Chan | A61K 47/12 |
| 2018/0207148 A1* | 7/2018 | Kwan | A61K 31/337 |

FOREIGN PATENT DOCUMENTS

| | | |
|---|---|---|
| JP | 2013541581 A | 11/2013 |
| TW | 201240664 | 10/2012 |
| WO | 9723208 | 7/1997 |
| WO | 9949848 | 10/1999 |

OTHER PUBLICATIONS

Definition of "oil". Accessed online on Jul. 1, 2022 at <https://www.merriam-webster.com/dictionary/oil>. (Year: 2022).*

"Polyoxyl castor oil". Accessed online on Jul. 1, 2022 at <https://www.imdcgroup.com>. (Year: 2022).*

\* cited by examiner

Figure 1.1A.
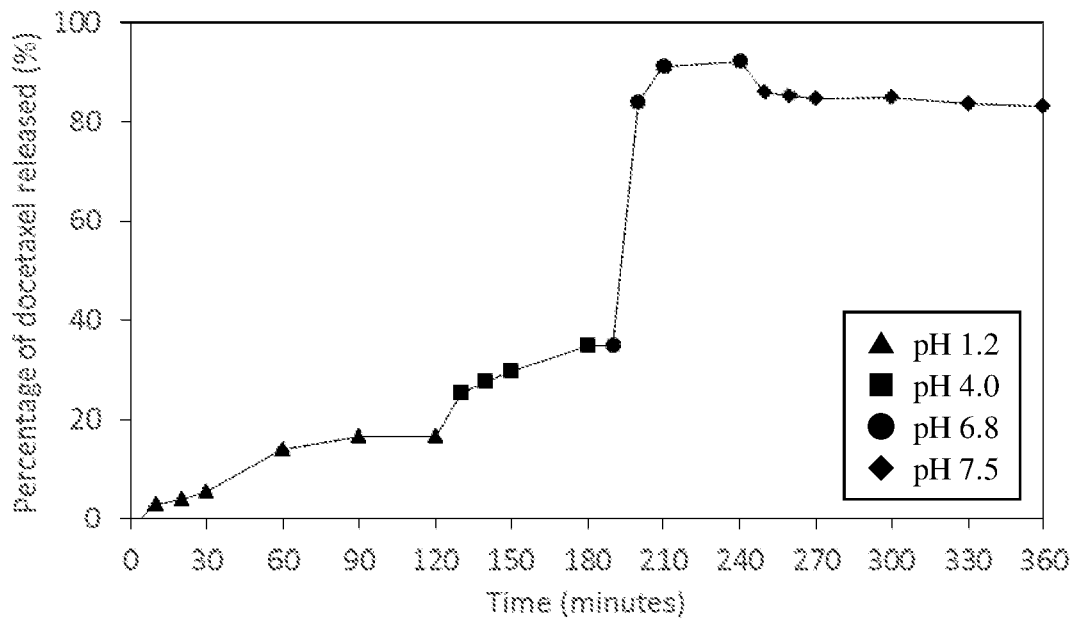
Figure 1.1B.
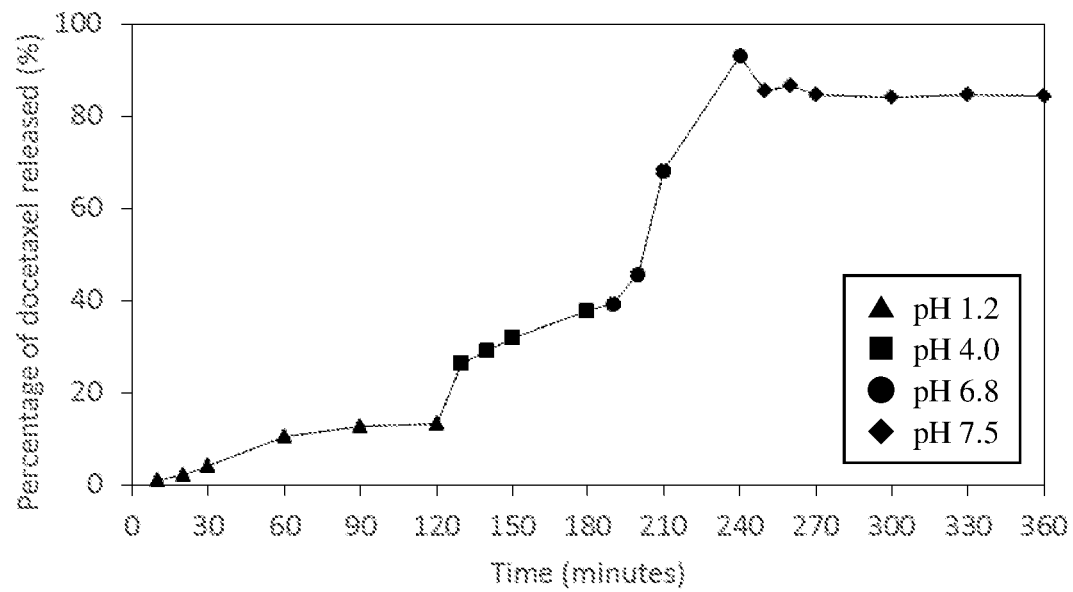

Figure 1.1C.
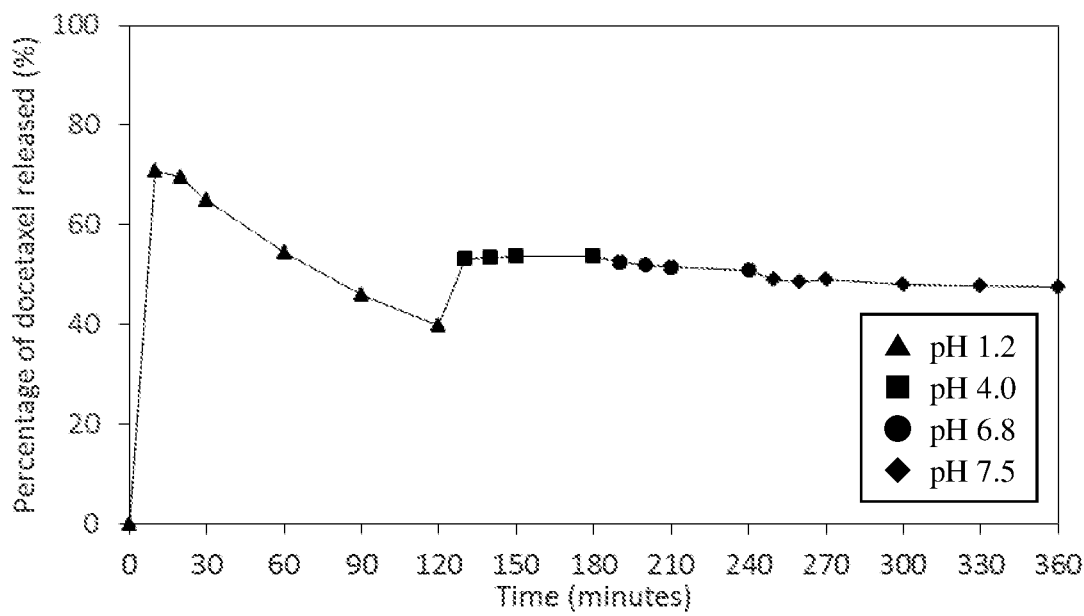
Figure 1.2A.
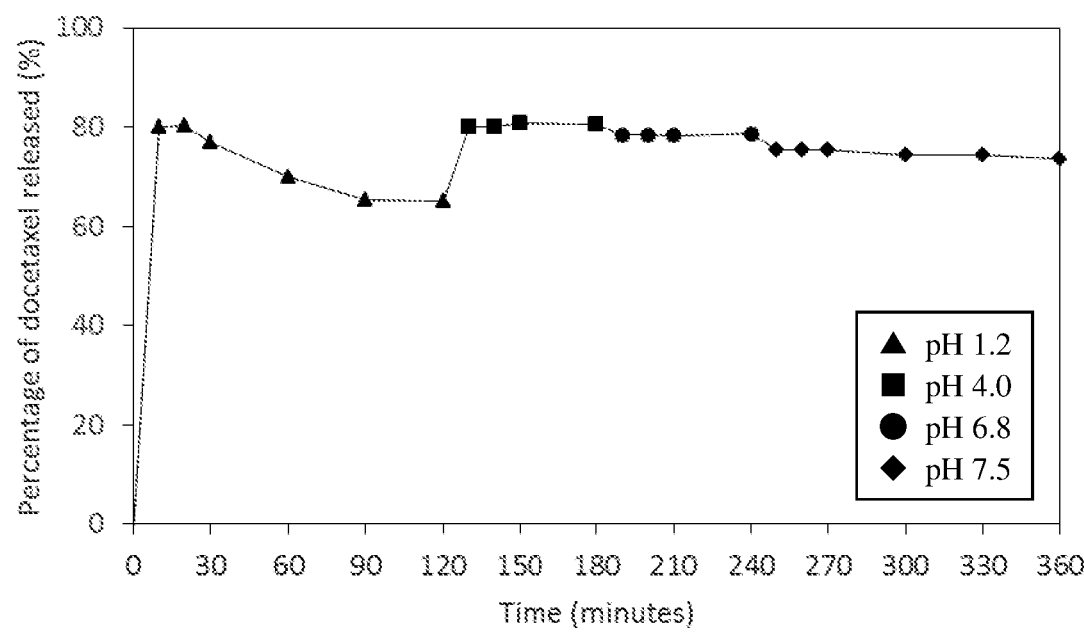

Figure 1.2B.
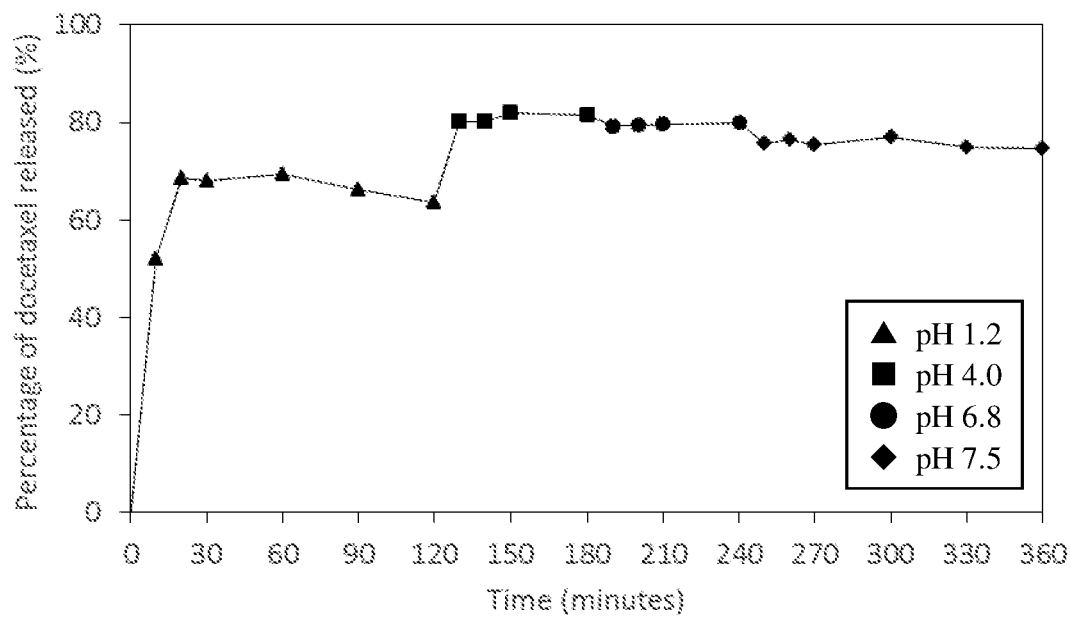
Figure 1.2C.
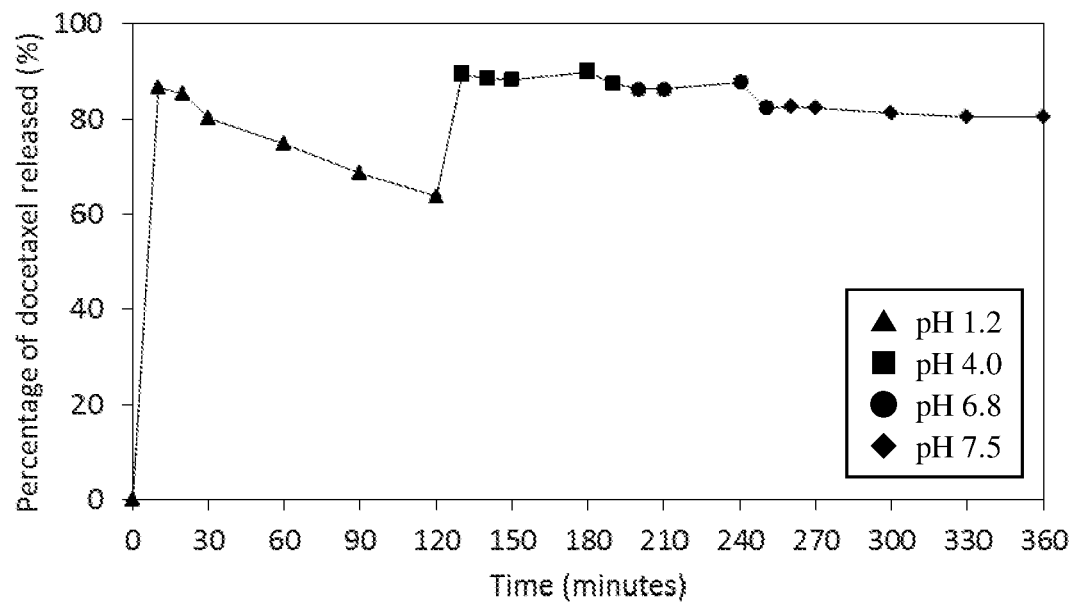

Figure 1.2D.
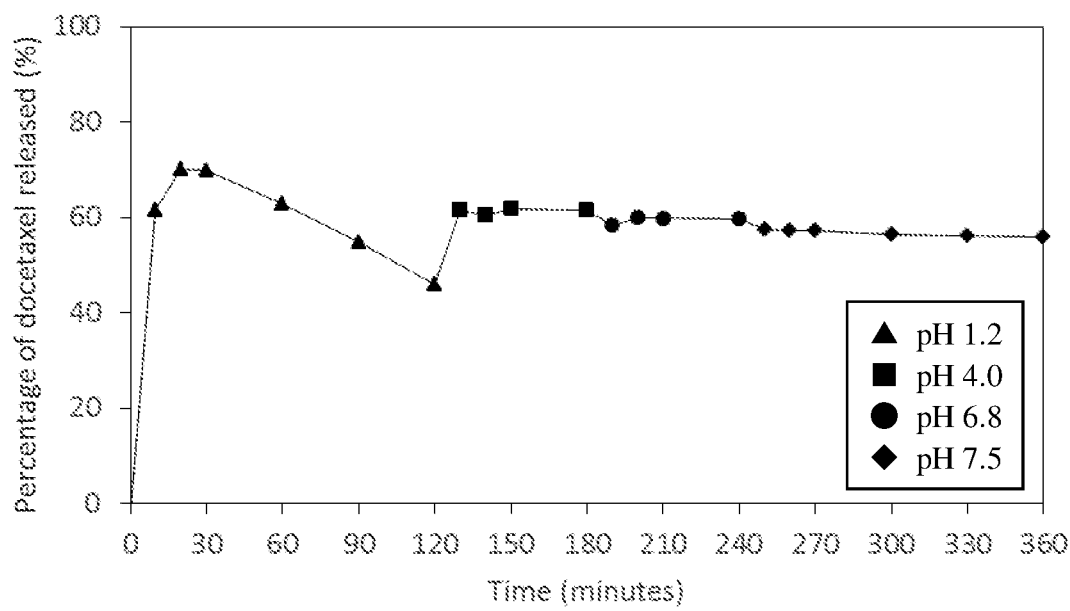
Figure 1.2E.
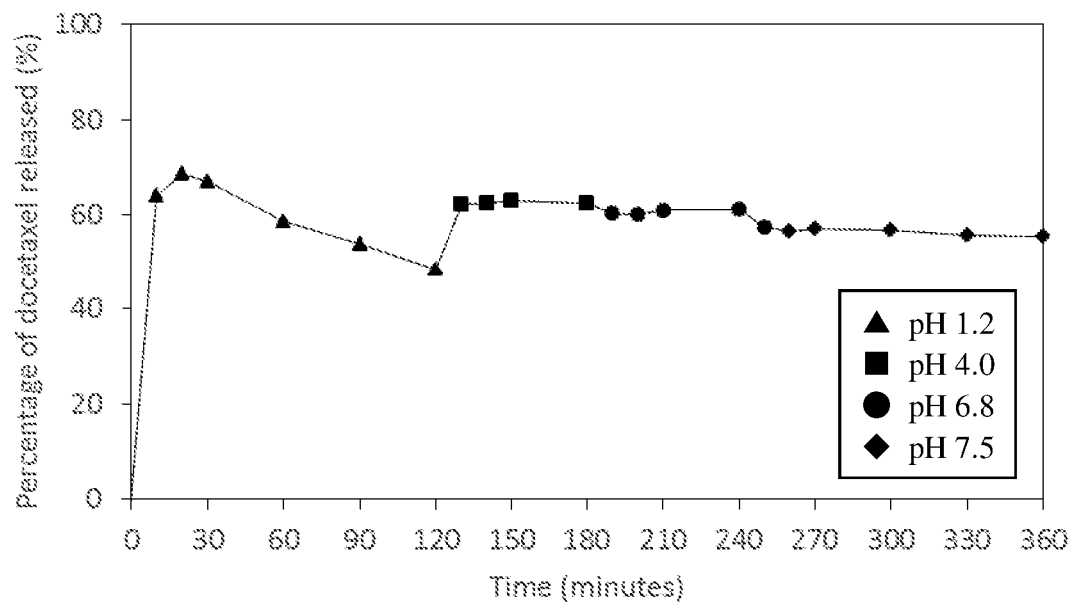

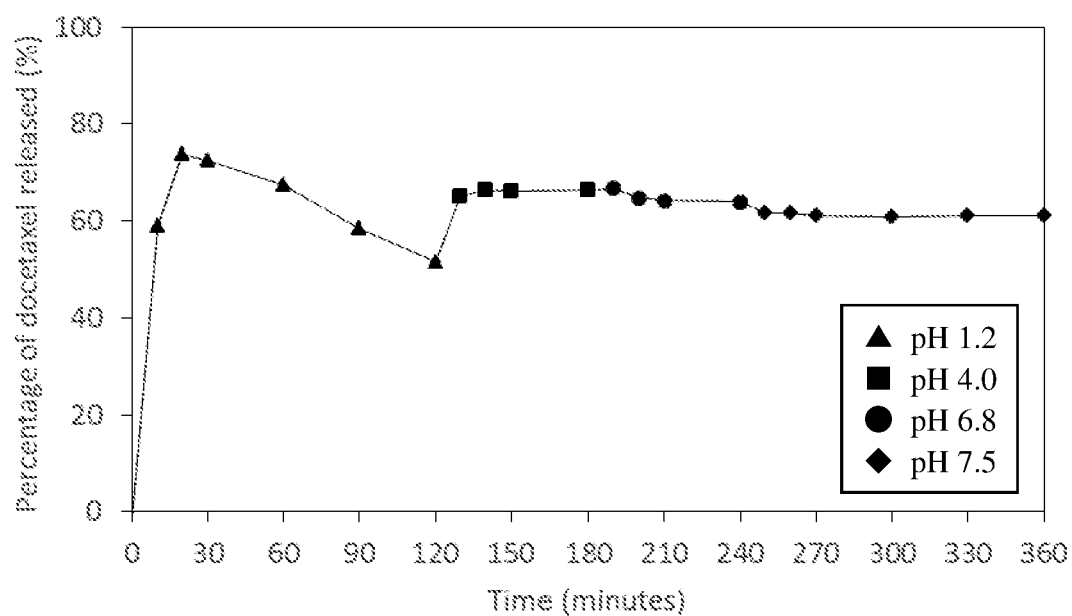
Figure 1.2F.

Figure 2.1.
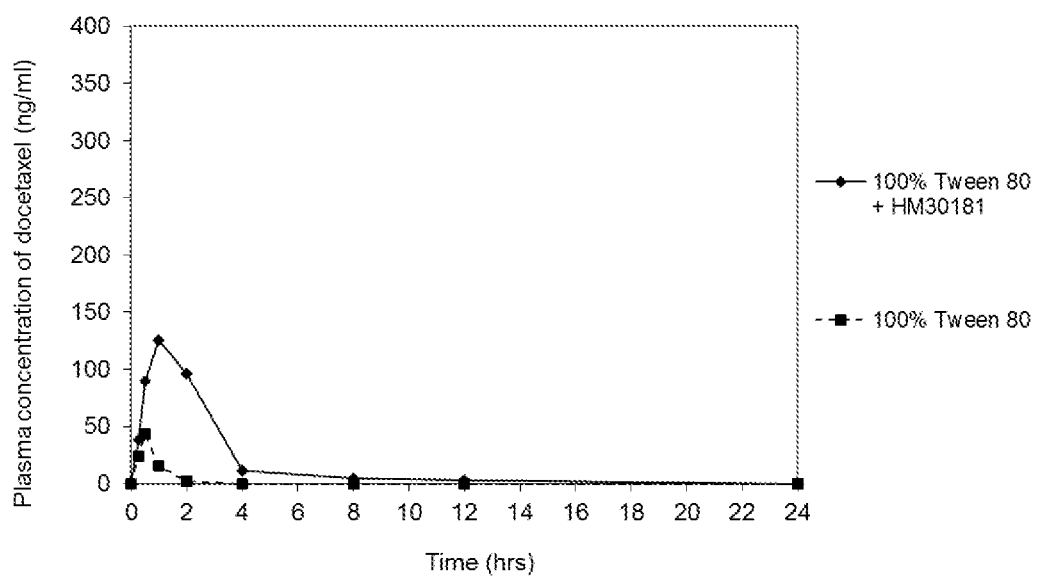
Figure 2.2.
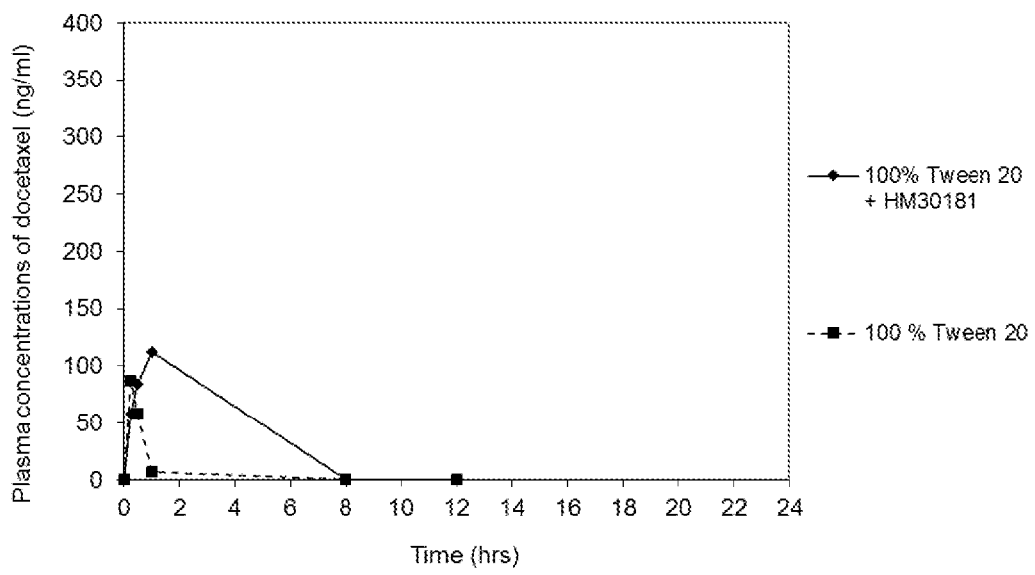

Figure 2.3.
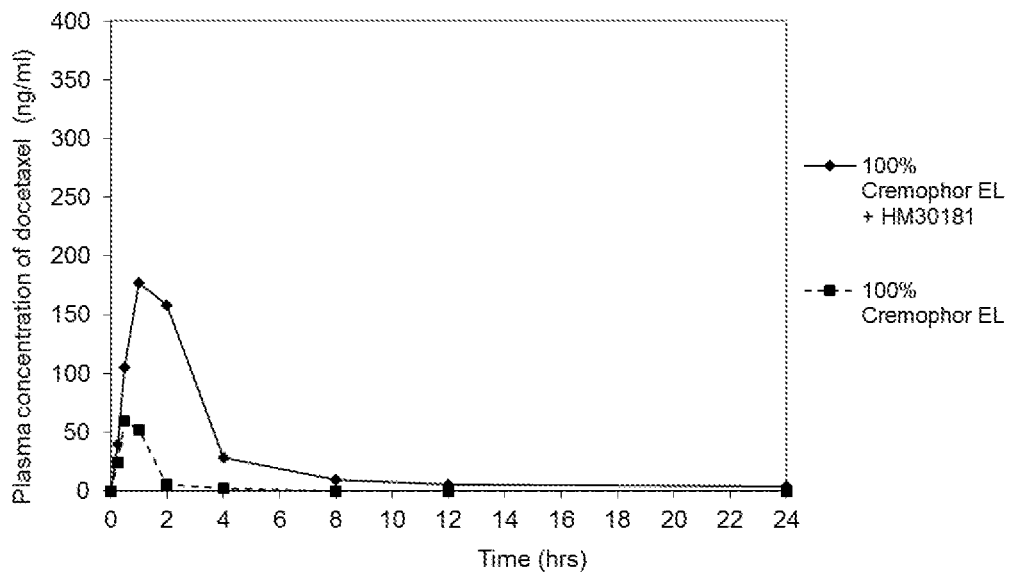
Figure 2.4.
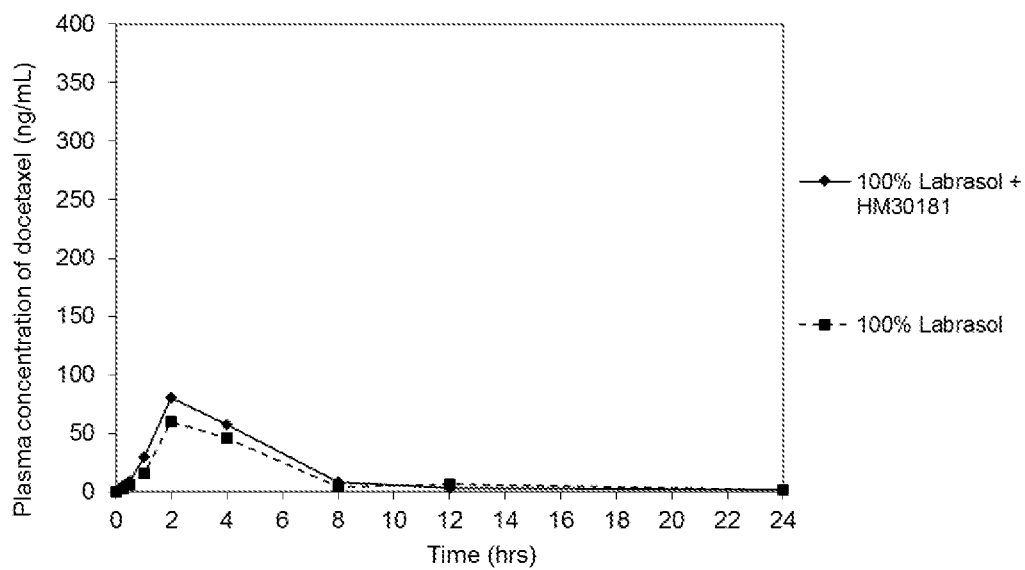

Figure 3.1.
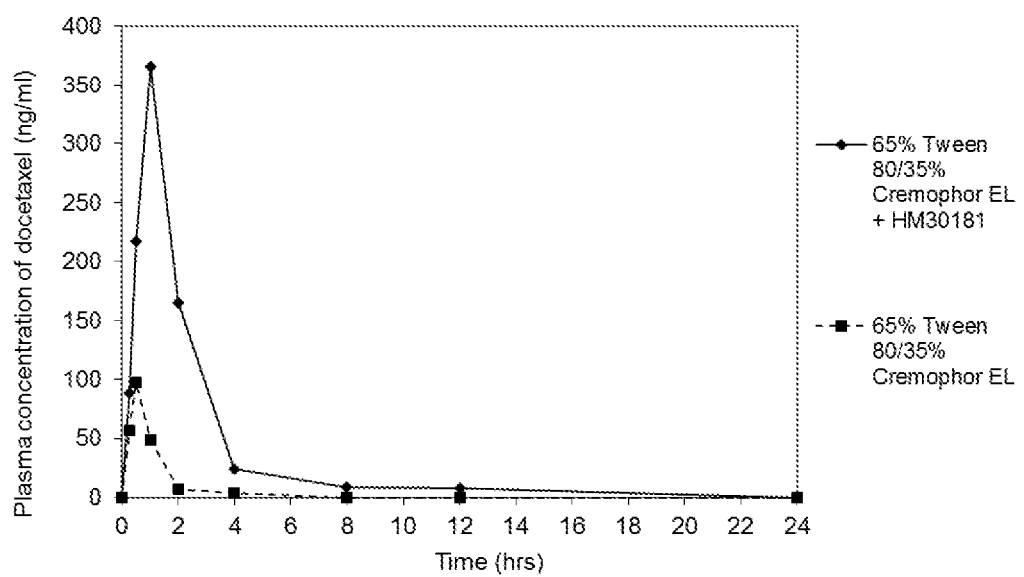

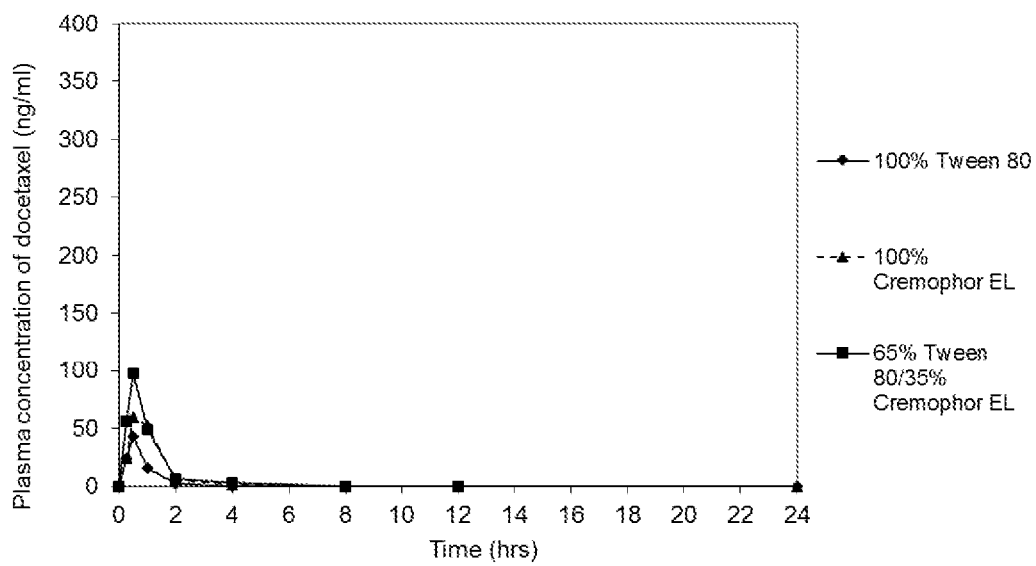
Figure 3.2A.
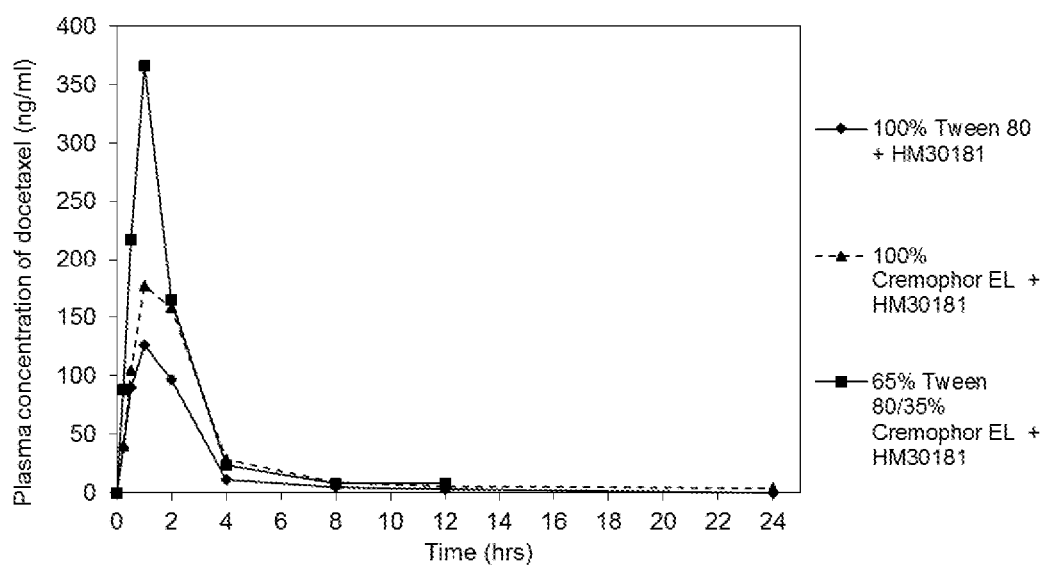
Figure 3.2B.

Figure 3.3A.
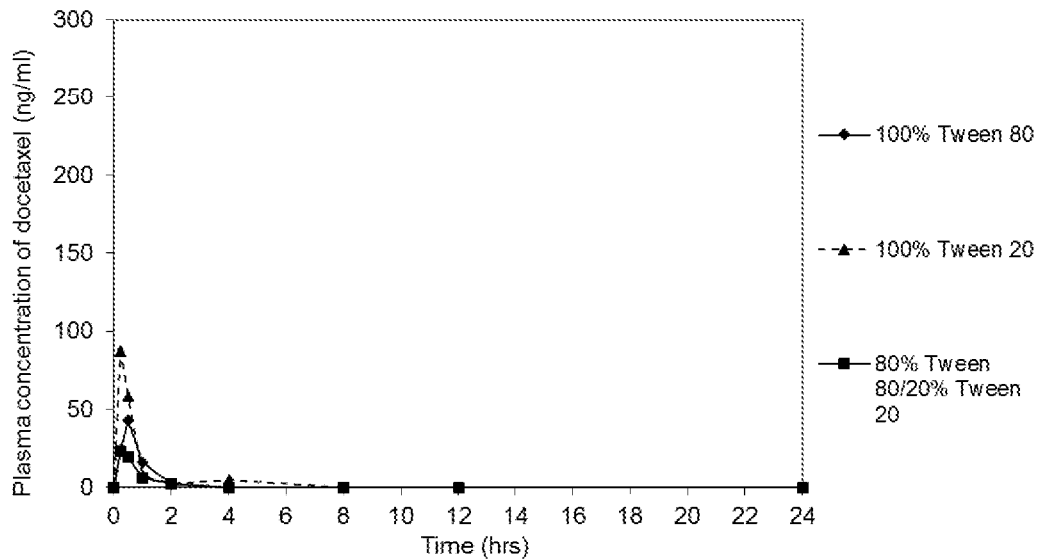
Figure 3.3B.
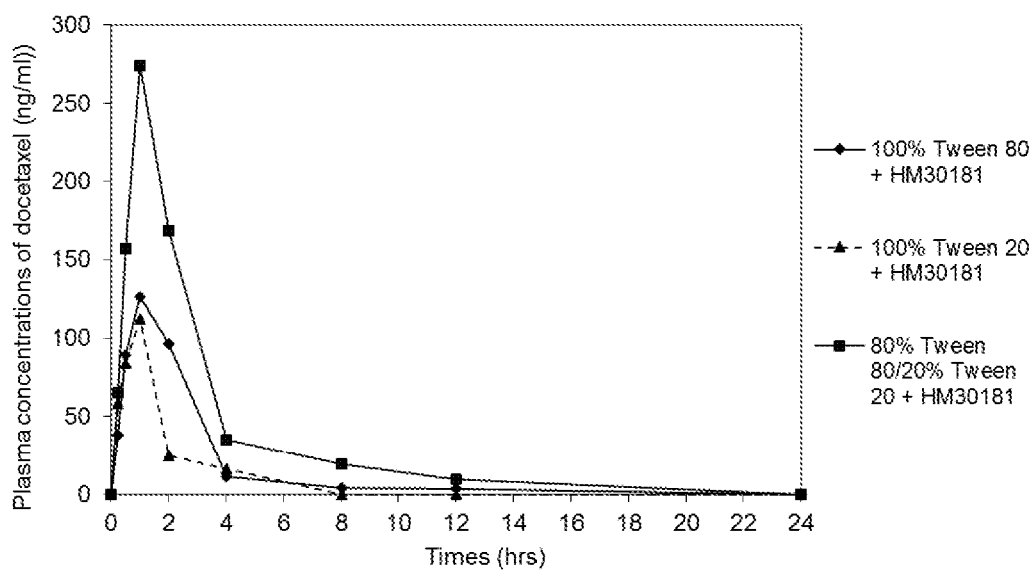

Figure 3.4A.
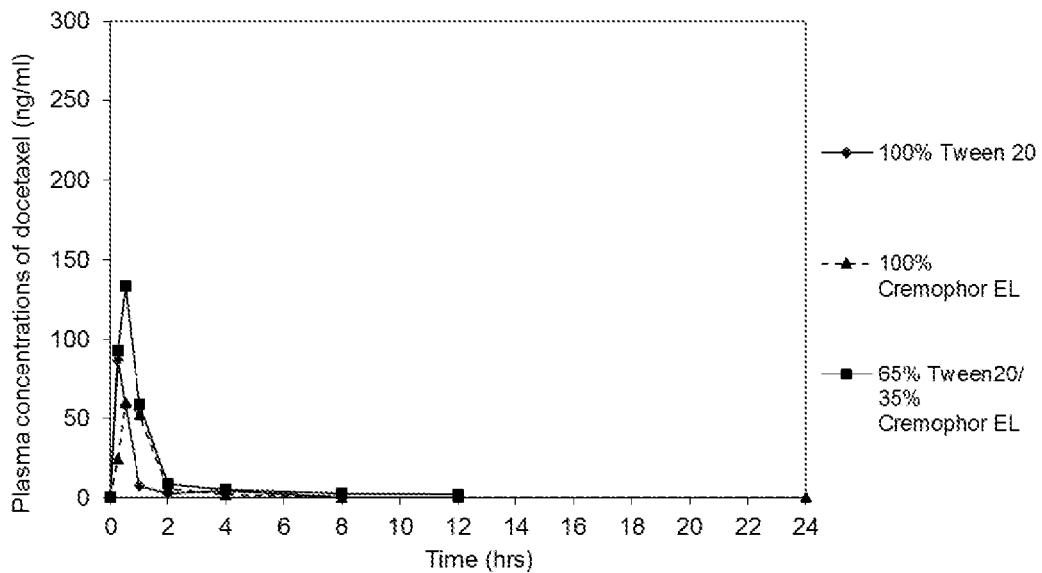
Figure 3.4B.
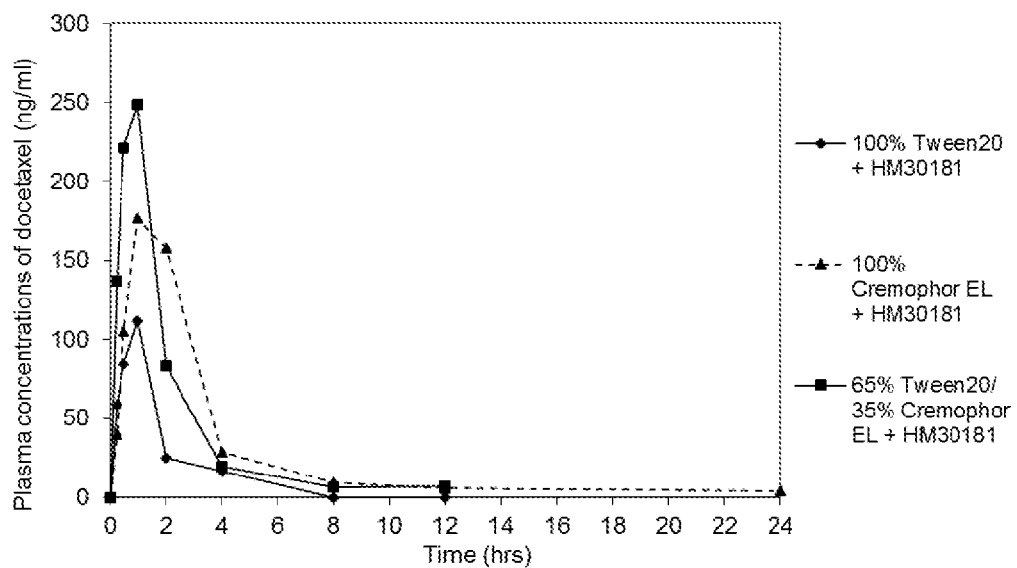

Figure 3.5A.
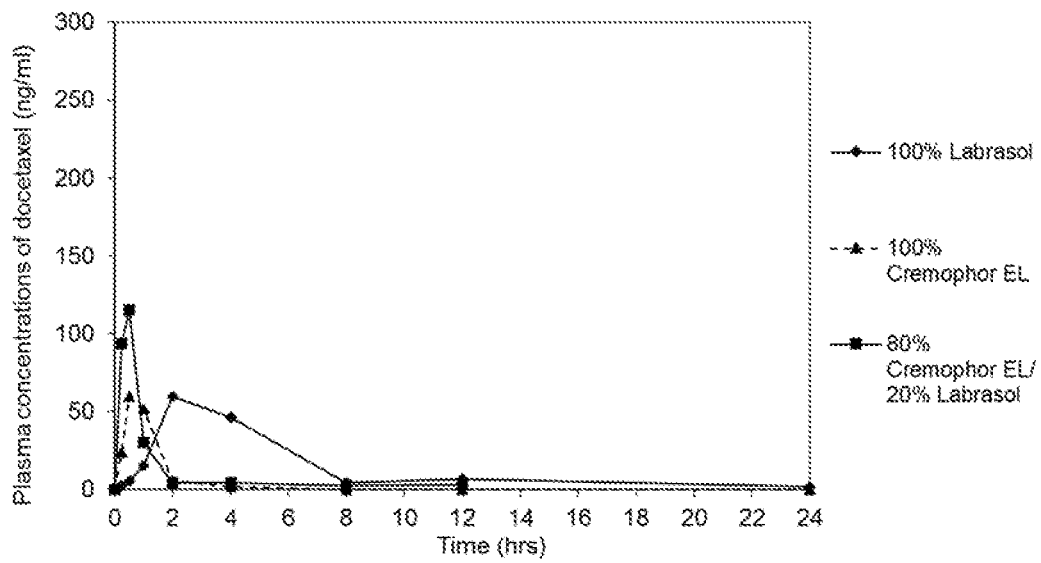
Figure 3.5B.
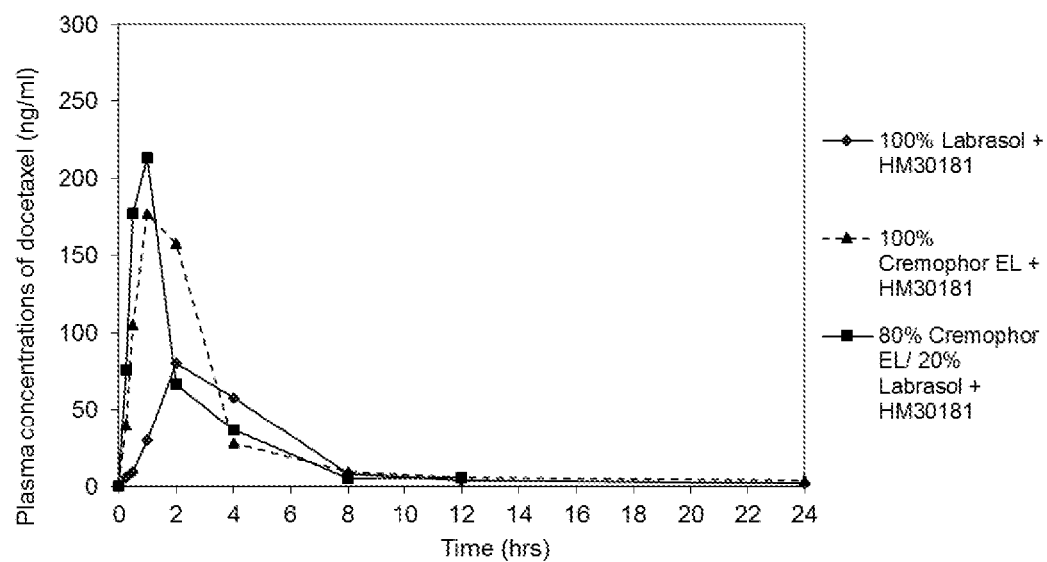

ORAL TAXANE COMPOSITIONS AND METHODS

This application is a continuation of U.S. patent application Ser. No. 15/277,890, filed Sep. 27, 2016, which claims the benefit of priority to U.S. Provisional Application 62/234,868 filed Sep. 30, 2015, the contents of which are incorporated by reference in their entireties. Where a definition or use of a term in a reference that is incorporated by reference is inconsistent or contrary to the definition of that term provided herein, the definition of the term provided herein is deemed to be controlling.

FIELD OF THE INVENTION

The field of the invention is pharmaceutical compositions and methods for oral delivery of taxanes at high bioavailability, typically achieved using combinations of distinct surfactants, optionally following administration or co-administration of a P-glycoprotein (PGP) inhibitor.

BACKGROUND

The following background discussion includes information that may be useful in understanding the present invention. It is not an admission that any of the information provided herein is prior art or relevant to the presently claimed invention, or that any publication specifically or implicitly referenced is prior art.

Taxanes are an important class of cytotoxic agents that includes paclitaxel (Taxol®), docetaxel (Taxotere® or Docecad), cabazitaxel, larotaxel, ortataxel, tesetaxel and the like. Paclitaxel is a diterpene isolated from the Pacific yew tree (*Taxus brevifolia*). Because paclitaxel binds tubulin, paclitaxel has the ability to inhibit cell division. Accordingly, paclitaxel has been approved for the treatment of ovarian, breast, lung, head and neck, and pancreatic cancers. Additionally, paclitaxel may effectively treat other maladies such as malaria and kidney disease. However, paclitaxel has a very low solubility in water, which makes formulating safe and effective therapies difficult.

In one known approach to improve solubility of taxanes for injectables, paclitaxel formulations include Cremophor® EL (Kolliphor® EL, polyoxyl 35 castor oil) or Tween® 80 (polysorbate 80) and ethanol. When administered in such formulations Cremophor® EL (or Tween® 80) are independently toxic and exhibit side effects such as vasodilation, hypotension, labored breathing, lethargy, anaphylactoid hypersensitivity reactions, hyperlipidemia, abnormal lipoprotein patterns, aggregation of erythrocytes, and peripheral neuropathy. One option to avoid these side-effects is to administer the pharmaceutical composition orally. Unfortunately, when administered orally, such paclitaxel formulations suffer from a very low bioavailability and absorption.

One reason for the low bioavailability of orally administered paclitaxel is that the paclitaxel formulations suffer from low physical stability in conditions found in the gastrointestinal (GI) tract. As used herein "physical stability" refers to the tendency for a taxane to remain dissolved in solution or to precipitate. A taxane with a high physical stability has a propensity to remain in solution, whereas a taxane with a low physical stability has a propensity to precipitate. Although pharmaceutical formulations initially contain dissolved taxanes, those taxanes readily precipitate in clinical settings, because paclitaxel is poorly soluble in water (solubility less than 0.01 mg/mL). Some water-miscible organic solvents partially dissolve paclitaxel. However, when the paclitaxel concentration is near saturation, diluting the solution with aqueous infusion fluid or stomach juices may cause the paclitaxel to precipitate. See U.S. Pat. No. 6,319,943 to Joshi et al. at col. 1, ln. 44 to col. 2, ln. 9; See U.S. Pat. No. 6,964,946 to Gutierrez-Rocca et al. at col. 10, ln. 39-65. Additionally, paclitaxel precipitates from Cremophor®/ethanol formulations upon dilution with infusion fluid. Paclitaxel precipitates even formed in some compositions during storage for extended periods of time. One strategy to prevent precipitation is to dissolve paclitaxel in an amphiphilic medium that forms micelles upon mixing with aqueous solutions. Advantageously, paclitaxel can remain solubilized in the interior of such micelles while the hydrophilic exterior keeps the micelles suspended in aqueous solutions. See U.S. Pat. No. 6,319,943 to Joshi et al. at col. 9, ln. 11-41. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Docetaxel is a derivative of paclitaxel, which is approved for the treatment of breast, lung, prostate, stomach, and head and neck cancers. Typically, docetaxel is again formulated with surfactants for parenteral delivery, and like paclitaxel, the bioavailability of orally administered docetaxel is very low. Another reason for the low bioavailability may be that the taxanes are effluxed from target cells by multidrug transporters, such as P-glycoprotein (PGP). To address this problem, attempts have been made to co-administer taxanes with PGP inhibitors. See, e.g., U.S. Pat. Nos. 6,245,805, 7,041,640 to Broder et al.; U.S. Pat. No. 7,115,565 to Gao et al. The compositions and methods closest to the inventive subject matter are disclosed in U.S. Pat. No. 6,964,946 to Gutierrez-Rocca et al. For example, Gutierrez-Rocca's pharmaceutical compositions comprise a taxane or taxane derivative, at least 30% by weight of a carrier, 0-70% a co-solubilizer. Gutierrez-Rocca also discloses methods in which such pharmaceutical compositions are administered to treat diseases. Optionally, a bioavailability enhancing agent, namely cyclosporine, can be administered up to 72 hours before or up to half an hour after administration of the taxane-containing pharmaceutical composition. Advantageously, Gutierrez-Rocca reports treatment regimens that resulted in paclitaxel plasma levels in the range of 50-500 ng/ml, which is comparable to the levels achieved during 96-hour IV infusion without the potential inconvenience, discomfort, lost time, and potential for infection. However, this system suffers from numerous disadvantages. Most notably the formulations are relatively complex and neglect to address the degradation of taxanes in the various carrier/co-solubilizer formulations and taxane precipitation upon contact with stomach fluids. See U.S. Pat. No. 6,319,943 to Joshi et al.; Int'l Pub. No. WO2007/085067 to Machado et al.

Therefore, even though certain formulations with improved bioavailability for taxanes have been produced, there is still a need to provide systems and methods for oral taxane compositions and methods with high bioavailability and solubility for taxanes.

SUMMARY OF THE INVENTION

The inventive subject matter provides compositions, methods and uses in which a taxane is formulated in a pharmaceutical composition with a combination of two surfactants, and most typically two chemically distinct surfactants. Preferably, the pharmaceutical composition is co-administered or administered after a PGP inhibitor (e.g., 4-oxo-4H-chromene-2-carboxylic acid [2-(2-(4-[2-(6,7-dimethoxy-3,4-dihydro-1H-isoquinolin-2-yl)-ethyl]-phenyl)-2H-tetrazol-5-yl)-4,5-dimethoxy-phenyl]-amide (HM30181)) is administered. Unexpectedly, absorption of the taxane following oral administration of the pharmaceutical composition is enhanced by more than the sum of the taxane absorbed when either surfactant is administered individually with the taxane. This synergistic effect is particularly observed when the surfactants are included in the pharmaceutical composition at specific ranges of ratios (e.g., from 60:40 to 85:15 by weight, inclusive of the endpoints). The recitation of ranges of values herein is merely intended to serve as a shorthand method of referring individually to each separate value falling within the range. Unless otherwise indicated herein, each individual value is incorporated into the specification as if it were individually recited herein.

Preferably, the ratio of the first surfactant to the second surfactant in the pharmaceutical composition is 65 (±2):35 (±2) or 80 (±2):20 (±2) by weight. In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. Generally, the weight of the first and second surfactants comprises no more than 90%, no more than 92%, no more than 94%, no more than 96%, or 98% of the total weight of the pharmaceutical composition.

With respect to the taxane, the inventors contemplate that paclitaxel, docetaxel, cabazitaxel, larotaxel, ortataxel, tesetaxel and the like are suitable for use in the inventive pharmaceutical compositions and methods. In preferred embodiments, the first surfactant comprises polysorbate 80 (Tween® 80), and the second surfactant is preferably polyoxyl 35 hydrogenated castor oil (Cremophor® EL), polyoxyl 40 hydrogenated castor oil (Cremophor® RH 40), or polysorbate 20 (Tween® 20). In further preferred embodiments, polysorbate 20 (Tween® 20) is the first surfactant, and the second surfactant is preferably a polyethyoxylated castor oil (e.g., Cremophor® EL or Cremophor® RH 40). In yet further preferred embodiments, the first surfactant comprises polyoxyl 35 hydrogenated castor oil (Cremophor® EL), and the second surfactant can be either caprylocaproyl polyoxylglycerides (Labrasol®) or polyoxyethylated 12-hydroxystearic acid (Solutol® HS 15). It should be appreciated that the pharmaceutical composition can further include a stabilizer such as citric acid and/or ascorbic acid (e.g., 0.1-5% by weight, preferably 0.5-1% by weight). The use of any and all examples, or exemplary language (e.g. "such as") provided with respect to certain embodiments herein is intended merely to better illuminate the invention and does not pose a limitation on the scope of the invention otherwise claimed.

Therefore, the inventors contemplate a kit comprising a PGP inhibitor and a pharmaceutical composition. The pharmaceutical composition includes a taxane and first and second surfactants. As described above, the first and second surfactants are present in respective amounts that enhance absorption of the taxane in more than an additive manner. The PGP inhibitor may be formulated for administration independent of the pharmaceutical composition. For example, the PGP inhibitor may be formulated as a pill to be taken orally one hour to five minutes before the pharmaceutical composition. Alternatively, the PGP inhibitor can be formulated for co-administration with the pharmaceutical composition.

In further aspects of the inventive subject matter, a method of producing a pharmaceutical composition includes formulating a taxane with first and second surfactants, wherein the first and second surfactants are present in respective amounts that enhance absorption of the taxane in more than an additive manner. In preferred methods, the first and second surfactants comprise no more than 90%, no more than 92%, no more than 94%, no more than 96%, or no more than 98% by weight of the pharmaceutical composition, and the weight ratio of the first surfactant to the second surfactant in the pharmaceutical composition is between 60:40 and 85:15.

Yet further aspects of the inventive subject matter include a method of treating a mammal by first providing an orally administered P-glycoprotein inhibitor to the mammal, and second providing an orally administered pharmaceutical composition as described above.

It should therefore be appreciated that methods of increasing at least one of taxane oral bioavailability and area under the curve for a taxane in an orally administered pharmaceutical composition can be attained by including first and second surfactants with a taxane in the orally administered pharmaceutical composition. Half-life, peak plasma concentration, and/or the time to reach the peak plasma concentration of the orally administered taxane may also increase.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1.1A is a graph showing the dissolution profile of docetaxel from a 100% Tween® 80 formulation at pH 1.2, pH 4.0, pH 6.8, and pH 7.5.

FIG. 1.1B is a graph showing the dissolution profile of docetaxel from a 100% Cremophor® EL formulation at pH 1.2, pH 4.0, pH 6.8, and pH 7.5.

FIG. 1.1C is a graph showing the dissolution profile of docetaxel from a 100% Tween® 20 formulation at pH 1.2, pH 4.0, pH 6.8, and pH 7.5.

FIG. 1.2A is a graph showing the dissolution profile of docetaxel from a 65% Tween® 80/35% Cremophor® EL formulation at pH 1.2, pH 4.0, pH 6.8, and pH 7.5.

FIG. 1.2B is a graph showing the dissolution profile of docetaxel from a 65% Tween® 80/35% Cremophor® RH 40 formulation at pH 1.2, pH 4.0, pH 6.8, and pH 7.5.

FIG. 1.2C is a graph showing the dissolution profile of docetaxel from an 80% Tween® 80/20% Tween® 20 formulation at pH 1.2, pH 4.0, pH 6.8, and pH 7.5.

FIG. 1.2D is a graph showing the dissolution profile of docetaxel from a 35% Tween® 20/65% Cremophor® EL formulation at pH 1.2, pH 4.0, pH 6.8, and pH 7.5.

FIG. 1.2E is a graph showing the dissolution profile of docetaxel from a 20% Labrasol®/80% Cremophor® EL formulation at pH 1.2, pH 4.0, pH 6.8, and pH 7.5.

FIG. 1.2F is a graph showing the dissolution profile of docetaxel from a 50% Cremophor® EL/50% Solutol® HS 15 formulation at pH 1.2, pH 4.0, pH 6.8, and pH 7.5.

FIG. 2.1 is a graph of plasma docetaxel concentration v. time after administration of a 100% Tween® 80 docetaxel formulation with and without co-administration of HM30181.

FIG. 2.2 is a graph of plasma docetaxel concentration v. time after administration of a 100% Tween® 20 docetaxel formulation with and without co-administration of HM30181.

FIG. 2.3 is a graph of plasma docetaxel concentration v. time after administration of a 100% Cremophor® EL docetaxel formulation with and without co-administration of HM30181.

FIG. 2.4 is a graph of plasma docetaxel concentration v. time after administration of a 100% Labrasol® docetaxel formulation with and without co-administration of HM30181.

FIG. 3.1 is a graph of plasma docetaxel concentration v. time after administration of a 65% Tween® 80/35% Cremophor® EL docetaxel formulation with and without co-administration of HM30181.

FIG. 3.2A is a graph of plasma docetaxel concentration v. time after administration of 100% Tween® 80, 100% Cremophor® EL, and 65% Tween® 80/35% Cremophor® EL docetaxel formulations (docetaxel administered alone).

FIG. 3.2B is a graph of plasma docetaxel concentration v. time after administration of 100% Tween® 80, 100% Cremophor® EL, and 65% Tween® 80/35% Cremophor® EL docetaxel formulations (docetaxel co-administered with HM30181).

FIG. 3.3A is a graph of plasma docetaxel concentration v. time after administration of 100% Tween® 80, 100% Tween® 20, and 80% Tween® 80/20% Tween® 20 docetaxel formulations (docetaxel administered alone).

FIG. 3.3B is a graph of plasma docetaxel concentration v. time after administration of 100% Tween® 80, 100% Tween® 20, and 80% Tween® 80/20% Tween® 20 docetaxel formulations (docetaxel co-administered with HM30181).

FIG. 3.4A is a graph of plasma docetaxel concentration v. time after administration of 100% Tween® 20, 100% Cremophor® EL, and 65% Tween® 20/35% Cremophor® EL docetaxel formulations (docetaxel administered alone).

FIG. 3.4B is a graph of plasma docetaxel concentration v. time after administration of 100% Tween® 20, 100% Cremophor® EL, and 65% Tween® 20/35% Cremophor® EL docetaxel formulations (docetaxel co-administered with HM30181).

FIG. 3.5A is a graph showing docetaxel plasma concentration v. time after administration of 100% Labrasol®, 100% Cremophor® EL, and 80% Cremophor® EL/20% Labrasol® docetaxel formulations (docetaxel administered alone).

FIG. 3.5B is a graph of plasma docetaxel concentration v. time after administration of 100% Labrasol®, 100% Cremophor® EL, and 80% Cremophor® EL/20% Labrasol® docetaxel formulations (docetaxel co-administered with HM30181).

DETAILED DESCRIPTION

The inventors surprisingly discovered that the bioavailability of orally administered taxanes, and particularly docetaxel, can be substantially increased by including a combination of two distinct surfactants in the taxane-containing pharmaceutical compositions. A synergistic increase in taxane bioavailability was unexpectedly observed when the ratio of the weights of the surfactants ranged from 60:40 to 85:15 by weight, inclusive of the endpoints. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

In preferred embodiments, the ratio of the first surfactant to the second surfactant in the pharmaceutical composition is about 65 (±2):35 (±2) or 80 (±2):20 (±2) by weight, and the total weight of the first and second surfactants comprises no more than 90%, no more than 92%, no more than 94%, no more than 96%, or no more than 98% by weight of the pharmaceutical composition. Typically, the pharmaceutical composition is administered after prior administration of a PGP inhibitor (e.g., prior administration between 5 min and 60 min, typically 20-40 min).

As used herein, taxanes include paclitaxel, docetaxel, cabazitaxel, larotaxel, ortataxel, tesetaxel and the like, and all pharmaceutically acceptable polymorphs, solvates, hydrates, etc. thereof. Likewise, suitable taxanes compounds will also include taxane prodrugs, precursors, derivatives, metabolites, and taxane conjugates (e.g., taxane-PEG, taxane-RGD, etc.). However, especially preferred embodiments include anhydrous docetaxel and docetaxel trihydrate in the pharmaceutical composition. Typically the concentration of the taxane in the pharmaceutical composition ranges from 0.1 to 90 mg/ml. More typically, the concentration of taxane is 5, 10, 15, 20, 25, 30, 35, 40, 45, 50, 55, 60, 65 or 70 mg/ml.

Exemplary surfactants include PEG esters, sucrose esters, polysorbates, tocopherol esters, pluronic block copolymers, vitamin E TPGS, Peceol™, Capryol™, Compritol®, Gelucire® surfactants, Geleol™, Geleil™, Pharmasolve™, and chitosan-tiobutylamidine. BASF sells surfactants for use in pharmaceutical preparations (http://www.pharma-ingredients.basf.com/Documents/ENP/Brochure/EN/Brochure_Solubilizer.pdf). Use of Kolliphor® TPGS and other Kolliphor® surfactants in the inventive pharmaceutical compositions are contemplated. Preferred surfactants Tween® 80 (polysorbate 80), Tween® 20 (polysorbate 20), Cremophor® EL (Kolliphor® EL, polyoxyl 35 hydrogenated castor oil), Cremophor® RH 40 (Kolliphor® RH 40, polyoxyl 40 hydrogenated castor oil), Solutol® HS 15 (Kolliphor® HS 15, polyoxyethylated 12-hydroxystearic acid), and Labrasol® (caprylocaproyl polyoxylglycerides).

To prevent taxane degradation, the pharmaceutical composition can further include a citric acid and/or ascorbic acid stabilizers. Other organic acids as described in Int'l Pub. No. WO2007/085067 to Machado et al. may also be employed. For example, malic acid, tartaric acid, lactic acid, tosilate, succinic acid, glutamic acid, alginic acid, maleic acid, and adipic acid may be substituted and/or added to the pharmaceutical composition.

The pharmaceutical composition may further comprise excipients such as water, ethanol, low molecular weight polyethylene glycols (e.g., PEG 200 and 400), starches/sugars, fats, and/or talc. Excipients may also include any of the water-soluble organic solvents, non-ionic surfactants, water-insoluble lipids, organic liquids/semisolids, cyclodextrins, and phospholipids described by Strickley in Solubilizing Excipients in Oral and Injectable Formulations, *Pharm. Res.*, vol. 21, no. 2, 201-229 (February 2004). The resulting pharmaceutical composition can be filled in hardgel or softgel capsules or administered in a liquid preparation.

To further enhance the bioavailability of the taxane, the inventive subject matter includes a kit comprising a PGP inhibitor and a pharmaceutical composition. Suitable PGP inhibitors include those disclosed by Srivalli and Lakshmi in Overview of P-glycoprotein inhibitors: a rational outlook, *Brazilian J. Pharm. Sci.*, vol 48, n. 3, pp. 353-367 (July/September 2012). For example, Verapamil, trifluoperazine, cyclosporine, other antihypertensives such as quinidine and reserpine, yohimbine, antiestrogenic, tamoxifen, toremifene, antineoplastic vincristine, and derivatives thereof may serve as suitable PGP inhibitors. Use of HM30181, XR9576, and GF120981 is also contemplated. Advantageously, HM30181 has been shown to increase the oral bioavailability and therapeutic efficacy of paclitaxel and was more potent than cyclosporine A. Kwak J.-O., Lee S. H., Kim, M. S. et al., Selective inhibition of MDR1 (ABCB1) by HM30181 increases oral bioavailability and therapeutic efficacy of paclitaxel, *Eur. J. Pharm.*, 627, 92-98 (2010). It should be appreciated that glycerol and PEG esters, sucrose esters, polysorbates, tocopherol esters, pluronic block copolymers, Peceol, Gelucire, and chitosan-tiobutylamidine may serve as both PGP inhibitors and surfactant (and/or excipient).

In one exemplary kit, the PGP inhibitor may be formulated as a pill to be taken orally up to 72 hours before and 72 hours after the pharmaceutical composition. More typically, the PGP inhibitor is administered a half hour before or at the same time as the pharmaceutical composition. Generally, PGP inhibitor formulations are consistent with the solid dispersions described in Int'l Pub. No. WO2014092489 to Kim et al.

The inventive subject matter also features methods of producing a pharmaceutical composition includes formulating a taxane with first and second surfactants. The taxane can be dissolved in a mixture of the first and second surfactants. Alternatively, the taxane can be dissolved in one surfactant, followed by addition of the other surfactant. Most typically, due to the relatively poor immediate solubilization, auxiliary measures can be taken and especially include heating, sonication, shearing, and/or extended periods of agitation (e.g., using stirrers). The respective quantities of the first and second surfactants are selected to enhance absorption of the taxane in more than an additive manner as is shown in more detail below. In preferred methods, the first and second surfactants comprise no more than 90%, no more than 92%, no more than 94%, no more than 96%, or no more than 98% by weight of the pharmaceutical composition, and the weight ratio of the first surfactant to the second surfactant in the pharmaceutical composition is between 60:40 and 85:15.

Mammals may be treated for various cancers and other taxane-responsive diseases in accordance with the methods of inventive subject matter. First, if desired, an orally administered P-glycoprotein inhibitor is provided to the mammal to generally increase net absorption. Second, an orally administered pharmaceutical composition as discussed herein is provided to the mammal once the P-glycoprotein inhibitor is administered, typically after about 30 minutes. It is contemplated that treatment with the inventive pharmaceutical compositions increase at least one of taxane oral bioavailability, half-life, peak plasma concentration, time to reach the peak plasma concentration, and area under the curve for a taxane in an orally administered pharmaceutical. Without wishing to be bound by a particular theory, one reason for the improvement in the pharmacokinetic properties of taxane when administered in the inventive pharmaceutical compositions may be that the surfactants form micelles when diluted in stomach/intestinal fluids. These micelles in turn are absorbed more favorably than taxanes administered in a single surfactant vehicle.

Experimental Results

1. Solubility and Physical Stability of Single-Surfactant and Two-Surfactant Docetaxel Formulations.

The maximum solubility of docetaxel in surfactant compositions is summarized in Table 1.1, below.

TABLE 1.1.

| Tween 80 (%) | Cremophor EL (%) | Maximum Solubility (mg/mL) | Maximum Solubility (mg/g) |
|---|---|---|---|
| 100 | 0 | 36.34 | 33.14 |
| 80 | 20 | 53.57 | 48.18 |
| 65 | 35 | 42.26 | 38.46 |
| 50 | 50 | 43.58 | 39.52 |
| 0 | 100 | 26.77 | 24.87 |

| Tween 80 (%) | Tween 20 (%) | Maximum Solubility (mg/mL) | Maximum Solubility (mg/g) |
|---|---|---|---|
| 100 | 0 | 36.34 | 33.14 |
| 80 | 20 | 43.34 | 38.98 |
| 65 | 35 | 42.74 | 39.53 |
| 50 | 50 | 44.85 | 39.89 |
| 0 | 100 | 55.2 | 50.2 |

| Tween 20 (%) | Cremophor EL (%) | Maximum Solubility (mg/mL) | Maximum Solubility (mg/g) |
|---|---|---|---|
| 100 | 0 | 55.2 | 50.2 |
| 50 | 50 | 53.9 | 50.14 |
| 35 | 65 | 44.76 | 39.08 |
| 20 | 80 | 42.41 | 38.46 |
| 0 | 100 | 26.77 | 24.87 |

| Labrasol (%) | Cremophor EL (%) | Maximum Solubility (mg/mL) | Maximum Solubility (mg/g) |
|---|---|---|---|
| 100 | 0 | 54.03 | 48.52 |
| 80 | 20 | 60.16 | 56.75 |
| 20 | 80 | 42.35 | 40.23 |
| 0 | 100 | 26.77 | 24.87 |

The solubility, physical stability and release of docetaxel in the single-surfactant and two-surfactant formulations were investigated using the USP 2011 dissolution apparatus II (Copley, UK) using 400 ml of dissolution medium equilibrated at 37±0.5° C. In order to simulate the changing pH conditions and transit times along the gastrointestinal tract, the following exemplary dissolution testing method was used:

a. Fill 650 mg liquid formulation in size 0 gelatin capsule.

b. Set stirring speed of dissolution paddle to 100 rotations per minute (rpm).

c. Introduce the capsule (in a sinker device) in the dissolution vessel containing 400 ml of pH 1.2 dissolution medium (0.1N HCl) for 2 hours, adjusted to pH 4.0 (by adding 100 ml 0.25 M $KH_2PO_4$ and 20% KOH; the resulting concentration of $KH_2PO_4$ is 50 mM) for 1 hour, and then adjusted to pH 6.8 (by adding KOH) for 1 hour and then pH 7.5 (by adding KOH) for 2 hours.

d. Collect samples at the following time-points: 0, 10, 20, 30, 60, 90 and 120 minutes for pH 1.2; 10, 20, 30 and 60 minutes for pH 4; 10, 20, 30 and 60 minutes for pH 6.8 and: 0, 10, 20, 30, 60, 90 and 120 minutes for pH 7.5. Replace an equivalent volume of fresh dissolution medium to compensate for loss due to each sampling.

e. Collected samples are centrifuged and the supernatants were used for HPLC analysis.

HPLC conditions for analysis of docetaxel in liquid formulations in dissolution testing.
  Dilution of Liquid Formulation (Methanol=1:30)
  Analytical Conditions:
  Instrument: Agilent 1260 Infinity
  Chromatographic parameters:
    Column: Zorbax Eclipse Plus C18, 4.6*150 mm, 5 μm
    Mobile phase: 0.2% Formic acid in water (A); Acetonitrile (B) (see Table 1.2)
    Flow rate: 0.8 ml/min
    Column temperature: 25° Celsius
    Injection volume: 20 μl
    Detection wavelength: 230 nm

TABLE 1.2.

| Time (minutes) | Solution A (%) | Solution B (%) |
|---|---|---|
| 0 | 80 | 20 |
| 3 | 70 | 30 |
| 11 | 30 | 70 |
| 17 | 30 | 70 |
| 18 | 0 | 100 |
| 25 | 0 | 100 |
| 26 | 30 | 70 |
| 30 | 30 | 70 |

FIGS. 1.1A, B and C show the release profiles of docetaxel from single-surfactant formulations: 100% Tween® 80, 100% Cremophor® EL, and 100% Tween® 20 formulations, respectively. FIGS. 1.1A and B show that the release of docetaxel was slow at pH 1.2 and pH 4, reaching maximum release after more than 210 minutes. While FIG. 1.1C shows that docetaxel release was initially quicker, the % release dropped quickly to 50% indicating that the docetaxel had precipitated in the dissolution media.

FIGS. 1.2 A-F show the dissolution release profiles of docetaxel from mixed-surfactant formulations comprising combinations of Tween® 80, Tween® 20, Cremophor® EL, Cremophor® RH 40, Solutol® HS 15, and Labrasol®. With all the combination formulations, the maximum concentrations were achieved within 30 minutes, and higher steady-state releases between 60 to 80% were maintained.

2. Bioavailability of Docetaxel from Single-Surfactant Formulations with and without Co-Administration of HM30181.

Sprague Dawley® rats were dosed by oral gavage with either docetaxel (20 mg/kg) alone or docetaxel (20 mg/kg) co-administered with HM30181 (10 mg/kg, 30 minutes prior to docetaxel) in various single-surfactant formulations. Each formulation was tested in a group of at least 3 rats (weighing around 180 to 350 g). Blood samples were collected via the jugular vein cannula prior to dosing and at 0.25, 0.5, 1.0, 2, 4, 8, 12 and 24 hours. Another group of 3 rats were received an intravenous dose of docetaxel (5 mg/kg) using the commercially available docetaxel injection (Taxotere®, Sanofi) for calculation of relative docetaxel bioavailability. The pharmacokinetic data improved when docetaxel was co-administered with HM30181 (i.e., a half hour after administration of HM30181) as evidenced by increases in the maximum plasma concentration (Cmax), area under curve (AUC), and docetaxel bioavailability (F). Time taken to reach the maximum plasma concentration (Tmax), mean residence time (MRT), and half-life ($t_{1/2}$) are also reported in the tables below.

FIG. 2.1 shows the plasma concentrations of docetaxel after administration of docetaxel in Tween® 80 alone and when co-administered with HM30181. As shown in Table 2.1, Tmax, Cmax, AUC, MRT, $t_{1/2}$, and docetaxel bioavailability increased by up to an order of magnitude.

TABLE 2.1

| Formulations | Tmax (h) | Cmax (ng/mL) | AUC0-t (h · ng/mL) | AUC0-∞ (h · ng/mL) | MRT (h) | t½ (h) | F (%) |
|---|---|---|---|---|---|---|---|
| 100% Tween 80 + HM30181 | 1.3 | 134.0 | 357.0 | 378.0 | 3.0 | 4.7 | 12.3 |
| 100% Tween 80 | 0.5 | 43.7 | 34.5 | 36.3 | 0.7 | 0.4 | 1.2 |

FIG. 2.2 shows the plasma concentrations of docetaxel after administration of docetaxel in Tween® 20 alone and when co-administered with HM30181. As shown in Table 2.2, Cmax, AUC, and docetaxel bioavailability increased.

TABLE 2.2

| Formulations | $T_{max}$ (h) | $C_{max}$ (ng/mL) | $AUC_{0-t}$ (h · ng/mL) | $AUC_{0-\infty}$ (h · ng/mL) | MRT (h) | $t_{1/2}$ (h) | F (%) |
|---|---|---|---|---|---|---|---|
| 100% Tween 20 + HM30181 | 0.8 | 114.0 | 240.0 | 253.0 | 2.0 | 2.3 | 8.3 |
| 100% Tween 20 | 0.3 | 87.2 | 62.8 | 92.5 | 1.3 | 4.9 | 2.2 |

FIG. 2.3 shows the plasma concentrations of docetaxel after administration of docetaxel in Cremophor® EL alone and when co-administered with HM30181. As shown in Table 2.3, Cmax increased threefold. AUC and docetaxel bioavailability increased approximately eightfold. That these results are comparable to the data obtained for polysorbate 80 docetaxel formulations is surprising in view of recent articles that reported that paclitaxel formulated in Cremophor® EL and ethanol exhibited lower oral bioavailability than paclitaxel formulated in polysorbate 80 and ethanol. M M Malingré et al., *The co-solvent Cremophor EL limits absorption of orally administered paclitaxel in cancer patients,* 85(10) BRITISH JOURNAL OF CANCER 1472, 1472-77 (2001); H A Bardelmeijer et al., *Entrapment by Cremophor EL decreases the absorption of paclitaxel from the gut,* 49 CANCER CHEMOTHER PHARMACOL 119, 119-25 (2002). The authors hypothesized that Cremophor® EL lowers Cmax, AUC, and absorption of paclitaxel by encapsulating both paclitaxel and cyclosporine A in micelles, which are poorly absorbed by the small intestine.

TABLE 2.3

| Formulations | Tmax (h) | Cmax (ng/mL) | AUC0-t (h · ng/mL) | AUC0-∞ (h · ng/mL) | MRT (h) | $t^{1/2}$ (h) | F (%) |
|---|---|---|---|---|---|---|---|
| 100% Cremophor EL + HM30181 | 1.3 | 182.0 | 608.0 | 608.0 | 3.9 | 15.4 | 21.0 |
| 100% Cremophor EL | 0.7 | 62.9 | 76.7 | 79.8 | 0.9 | 0.7 | 2.6 |

FIG. 2.4 shows the plasma concentrations of docetaxel after administration of docetaxel in Labrasol® alone and when co-administered with HM30181. The effect of HM30181 was modest in comparison with the results obtained using Labrasol® as a vehicle. As shown in Table 2.4, Cmax, AUC, and docetaxel bioavailability increased.

TABLE 2.4

| Formulations | $T_{max}$ (h) | $C_{max}$ (ng/mL) | $AUC_{0-t}$ (h · ng/mL) | $AUC_{0-\infty}$ (h · ng/mL) | MRT (h) | $t_{1/2}$ (h) | F (%) |
|---|---|---|---|---|---|---|---|
| 100% Labrasol + HM30181 | 2.7 | 81.7 | 361.0 | 372.0 | 5.8 | 5.6 | 12.5 |
| 100% Labrasol | 2.7 | 63.9 | 289.0 | 302.0 | 6.2 | 5.9 | 10.0 |

3. Bioavailability of Docetaxel from Two-Surfactant Formulations with and without Co-Administration of HM30181.

Sprague Dawley® rats were dosed by oral gavage with either docetaxel (20 mg/kg) alone or docetaxel (20 mg/kg) co-administered with HM30181 (10 mg/kg, 30 minutes prior to docetaxel) in various two-surfactant formulations (in differing weight ratios). Each formulation was tested in a group of at least 3 rats (weighing around 180 to 350 g). Blood samples were collected via the jugular vein cannula prior to dosing and at 0.25, 0.5, 1.0, 2, 4, 8, 12 and 24 hours. Another group of 3 rats were received an intravenous dose of docetaxel (5 mg/kg) using the commercially available docetaxel injection (Taxotere®, Sanofi) for calculation of relative docetaxel bioavailability. The pharmacokinetic data improved when HM30181 was co-administered with HM30181 (i.e., a half hour after administration of HM30181) as evidenced by increases in the maximum plasma concentration (Cmax), area under curve (AUC), and docetaxel bioavailability (F). Time taken to reach the maximum plasma concentration (Tmax), mean residence time (MRT), and half-life ($t_{1/2}$) are also reported in the tables below.

FIG. 3.1 shows the increase in plasma concentrations of docetaxel when docetaxel is administered in Tween® 80 and Cremophor® EL (65% and 35% by weight, respectively) after co-administration of HM30181. As shown in Table 3.1, Cmax, AUC, and docetaxel bioavailability increased.

TABLE 3.1

| Formulations | Tmax (h) | Cmax (ng/mL) | AUC0-t (h · ng/mL) | AUC0-∞ (h · ng/mL) | MRT (h) | t½ (h) | F (%) |
|---|---|---|---|---|---|---|---|
| 65% Tween 80/35% Cremophor EL + HM30181 | 1.0 | 366.0 | 746.0 | 809.0 | 2.1 | 5.9 | 25.8 |
| 65% Tween 80/35% Cremophor EL | 0.5 | 97.6 | 118.0 | 133.0 | 1.6 | 4.5 | 4.1 |

FIGS. 3.2A shows the plasma concentrations of docetaxel after administration of docetaxel formulated in Tween® 80 only, Cremophor® EL only, and 65% Tween® 80/35% Cremophor® EL. FIG. 3.2B shows the plasma concentrations of docetaxel after administration of the docetaxel formulations with co-administration of HM30181. As can be seen in both FIGS. 3.2A and B, the plasma concentrations of docetaxel after administration of docetaxel in 65% Tween® 80/35% Cremophor® EL modestly exceeds the plasma concentrations achieved when docetaxel is formulated in Tween® 80 and Cremophor® EL individually. Co-administration of docetaxel in 65% Tween® 80/35% Cremophor® EL with HM30181 resulted in a 3.75 fold increase in Cmax as compared to the Cmax observed when docetaxel in 65% Tween® 80/35% Cremophor® EL was administered alone.

Table 3.2 shows the effect of varying the ratio between the weight of Tween® 80 and Cremophor® EL on Tmax, Cmax, AUC, MRT, $t_{1/2}$, and bioavailability, when docetaxel was administered alone and co-administered with HM30181. In this experiment, the highest AUC and docetaxel bioavailability values were observed when the ratio of Tween® 80 to Cremophor® EL was 65% to 35% by weight.

TABLE 3.2

| Formulations | Tmax (h) | Cmax (ng/mL) | AUC0-t (h · ng/mL) | AUC0-∞ (h · ng/mL) | MRT (h) | t½ (h) | F (%) |
|---|---|---|---|---|---|---|---|
| Without HM30181 | | | | | | | |
| 100% Tween 80 | 0.5 | 43.7 | 34.5 | 36.3 | 0.7 | 0.4 | 1.2 |
| 80% Tween 80/20% Cremophor EL | 0.5 | 67.8 | 86.8 | 94.6 | 1.9 | 1.8 | 3.0 |
| 65% Tween 80/35% Cremophor EL | 0.5 | 97.6 | 118.0 | 133.0 | 1.6 | 4.5 | 4.1 |
| 50% Tween 80/50% Cremophor EL | 0.4 | 47.5 | 42.1 | 52.1 | 0.8 | 0.9 | 1.5 |
| 100% Cremophor | 0.7 | 62.9 | 76.7 | 79.8 | 0.9 | 0.7 | 2.6 |
| With HM30181 | | | | | | | |
| 100% Tween 80 | 1.3 | 134.0 | 357.0 | 378.0 | 3.0 | 4.7 | 12.3 |
| 80% Tween 80/20% Cremophor EL | 1.2 | 67.4 | 198.7 | 214.9 | 1.9 | 2.0 | 6.9 |
| 65% Tween 80/35% Cremophor EL* | 1.0 | 366.0 | 746.0 | 809.0 | 2.1 | 5.9 | 25.8 |
| 50% Tween 80/50% Cremophor EL | 1.0 | 189.0 | 599.0 | 671.3 | 2.7 | 4.9 | 20.7 |
| 100% Cremophor | 1.3 | 182.0 | 608.0 | 608.0 | 3.9 | 15.4 | 21.0 |

*optimal Tween 80/Cremophor EL ratio

FIGS. 3.3A and B show the plasma concentrations of docetaxel after administration of docetaxel in 100% Tween® 80, 100% Tween® 20, and 80% Tween® 80/20% Tween® 20 formulations. Each pharmaceutical composition was tested without (FIG. 3.3A) and with (FIG. 3.3B) co-administration of HM30181. As can be seen FIG. 3.3B, the plasma concentrations of docetaxel after administration of docetaxel in 80% Tween® 80/20% Tween® 20 when co-administered with HM30181 exceeds the plasma concentrations achieved when docetaxel is formulated in Tween® 80 and Tween® 20 individually.

Table 3.3 shows the effect of varying the ratio between the weight of Tween® 80 and Tween® 20 on Tmax, Cmax, AUC, MRT, $t_{1/2}$, and bioavailability, when docetaxel was administered alone and co-administered with HM30181. In this experiment, the greatest AUC and docetaxel bioavailability values were observed when the ratio of Tween® 80 to Tween® 20 was 80% to 20% by weight.

TABLE 3.3

| Formulations | Tmax (h) | Cmax (ng/mL) | AUC0-t (h · ng/mL) | AUC0-∞ (h · ng/mL) | MRT (h) | t½ (h) | F (%) |
|---|---|---|---|---|---|---|---|
| Without HM30181 | | | | | | | |
| 100% Tween 80 | 0.5 | 43.7 | 34.5 | 36.3 | 0.7 | 0.4 | 1.2 |
| 80% Tween 80/20% Tween 20 | 0.4 | 26.1 | 28.3 | 41.3 | 1.5 | NA | 1.0 |
| 65% Tween 80/35% Tween 20 | 0.9 | 11.8 | 13.6 | 9.0 | 0.9 | 0.5 | 0.5 |
| 100% Tween 20 | 0.3 | 87.2 | 62.8 | 92.5 | 1.3 | 4.9 | 2.2 |
| With HM30181 | | | | | | | |
| 100% Tween 80 | 1.3 | 134.0 | 357.0 | 378.0 | 3.0 | 4.7 | 12.3 |
| 80% Tween 80/20% Tween 20* | 1.0 | 274.0 | 737.0 | 800.7 | 2.8 | 4.4 | 25.4 |
| 65% Tween 80/35% Tween 20 | 1.0 | 41.2 | 138.0 | 188.0 | 5.3 | NA | 4.8 |
| 100% Tween 20 | 0.8 | 114.0 | 240.0 | 253.0 | 2.0 | 2.3 | 8.3 |

*optimal Tween 80/Tween 20 ratio

FIG. 3.4A shows the plasma concentrations of docetaxel after administration of 100% Tween® 20®, 100% Cremophor® EL, and 65% Tween® 20/35% Cremophor® EL docetaxel formulations. FIG. 3.4B shows the plasma docetaxel concentrations after administration of each docetaxel formulation with co-administration of HM30181. As can be seen FIG. 3.4A, the plasma concentrations of docetaxel after administration of docetaxel in 65% Tween® 20/35% Cremophor® EL exceeds the plasma concentrations achieved when docetaxel is formulated in Tween® 20 and Cremophor® EL individually. FIGS. 3.4A and B clearly show that 65% Tween® 20/35% Cremophor® EL formulation achieved higher Cmax values than Tween® 20 only or Cremophor® EL only formulations.

FIGS. 3.5A and B show the plasma concentrations of docetaxel after administration of docetaxel in Labrasol®, Cremophor® EL, and 80% Labrasol®/20% Cremophor® EL. Each pharmaceutical composition was tested with and without co-administration of HM30181. It is evident that the Cmax values were higher when docetaxel was formulated in 80% Labrasol®/20% Cremophor® EL when compared to formulation with individual surfactants.

Thus, based on the above data, it should be readily apparent that the addition of a second distinct surfactant provided significantly more than additive effects on numerous pharmacokinetic parameters. A theoretical additive value can be calculated according to the following equation:

$$\text{Theoretical Additive Value} = \frac{(\%_{Surfactant\,1} \times Value_{100\%\,Surfactant\,1}) + (\%_{Surfactant\,2} \times Value_{100\%\,Surfactant\,2})}{100\%}.$$

A synergistic effect is observed when the measured value exceeds the theoretical additive value. Stated another way, the additive Cmax, AUC, and bioavailability (F) should be weighted based on the proportion of each surfactant in two-surfactant formulations. For example, using the data from Table 3.2 for 100% Tween® 80, 65% Tween® 80/35% Cremophor® EL, and 100% Cremophor® EL with co-administration of HM30181, the bioavailability (F) of docetaxel in 100% Tween® 80 was 12.3%; the 100% Cremophor® EL the bioavailability (F) was 21.0%; and the 65/35 Tween® 80/Cremophor® EL the F was 25.8%. So one might simplistically think that an additive effect would be 12.3% plus 21.0%, giving 33.3%. The observed 25.8% appears to be less than 33.3%, i.e., less than the incorrect additive value. This would be an incorrect analysis. The correct analysis is to imagine 65% of the standard amount of drug was administered in Tween® 80 and 35% in Cremophor® EL. The additive F then would be the weighted average, or 15.3%. The observed 25.8% is 1.68 times the additive F, clearly more than just additive and correctly labeled as synergistic. In another example using the data from Table 3.2 for 100% Tween® 80, 65% Tween® 80/35% Cremophor® EL, and 100% Cremophor® EL without co-administration of HM30181, a theoretical additive bioavailability (F) is 1.7%. The observed bioavailability is 4.1%, giving a 2.4-fold synergistic increase in bioavailability.

Table 3.4 summarizes theoretical AUC and oral bioavailability values derived from the data provided in Tables 3.2 and 3.3. It should be readily apparent that the data are unpredictable and show no trend in synergistic ratio as the proportion and identity of the surfactant formulations vary. Thus, the synergistic increase in AUC and bioavailability of docetaxel orally administered in 65% Tween® 80/35% Cremophor® EL (without and with co-administration of HM30181) is unexpected. Surprisingly, a synergistic increase in AUC and bioavailability was observed when docetaxel was orally administered in 65% Tween® 80/35% Tween® 20 with co-administration with HM30181, but not without co-administration of HM30181.

TABLE 3.4

| Tween 80 (%) | Cremophor EL (%) | AUC$_{0-\infty}$ (h · ng/mL) | | | F (%) | | |
|---|---|---|---|---|---|---|---|
| | | Actual | Theoretical | Synergistic Ratio | Actual | Theoretical | Synergistic Ratio |
| Without co-administration of HM30181 | | | | | | | |
| 100 | 0 | 36.3 | | | 1.2 | | |
| 80 | 20 | 94.6 | 45.0 | 2.10 | 3 | 1.48 | 2.03 |
| 65 | 35 | 133 | 51.5 | 2.58 | 4.1 | 1.69 | 2.43 |

TABLE 3.4-continued

| 50 | 50 | 52.1 | 58.1 | 0.898 | 1.5 | 1.90 | 0.789 |
|---|---|---|---|---|---|---|---|
| 0 | 100 | 79.8 | | | 2.6 | | |

With co-administration of HM30181

| 100 | 0 | 378 | | | 12.3 | | |
|---|---|---|---|---|---|---|---|
| 80 | 20 | 214.9 | 424 | 0.507 | 6.9 | 14.0 | 0.491 |
| 65 | 35 | 809 | 459 | 1.76 | 25.8 | 15.3 | 1.68 |
| 50 | 50 | 671.3 | 493 | 1.36 | 20.7 | 16.7 | 1.24 |
| 0 | 100 | 608 | | | 21 | | |

| | | AUC$_{0-\infty}$ (h · ng/mL) | | | F (%) | | |
|---|---|---|---|---|---|---|---|
| Tween 80 (%) | Tween 20 (%) | Actual | Theoretical | Synergistic Ratio | Actual | Theoretical | Synergistic Ratio |

Without co-administration of HM30181

| 100 | 0 | 36.3 | | | 1.2 | | |
|---|---|---|---|---|---|---|---|
| 80 | 20 | 41.3 | 47.5 | 0.869 | 1.0 | 1.2 | 0.81 |
| 65 | 35 | 9 | 60 | 0.2 | 0.5 | 1.1 | 0.46 |
| 0 | 100 | 92.5 | | | 2.2 | | |

With co-administration of HM30181

| 100 | 0 | 378 | | | 12.3 | | |
|---|---|---|---|---|---|---|---|
| 80 | 20 | 800.7 | 353 | 2.27 | 25.4 | 11.5 | 2.21 |
| 65 | 35 | 188 | 334 | 0.562 | 4.8 | 10.9 | 0.440 |
| 0 | 100 | 253 | | | 8.3 | | |

Such finding is especially unexpected as, at least in theory, the mode of action of surfactants should be substantially the same. Addition of a second, distinct surfactant has thus the technical effect of synergistically increasing one or more pharmacokinetic parameters. Specifically, especially notable increases were observed where the first surfactant was Tween® 80, Tween® 20, or Labrasol®, and the second surfactant was Cremophor® EL or Tween® 20. The results presented herein are especially unexpected, because Malingré and Bardelmeijer, supra, teach that Cremophor® EL formulations decrease the bioavailability of orally administered paclitaxel.

In addition, especially advantageous increases in the one or more pharmacokinetic parameters could be observed where the weight ratios of first and second surfactants were relatively balanced, typically in a range of between 60:40 and 85:15.

4. Exemplary Method of Preparing a Liquid Pharmaceutical Composition Having a Docetaxel Concentration of 45 mg/ml (64.35% Tween® 80, 34.65% Cremophor® EL, 0.5% Ascorbic Acid, 0.5% Citric Acid):

a. Accurately weigh 1.95 g Tween® 80 and 1.05 g Cremophor® EL into 20 ml glass vial.
b. Mix thoroughly by magnetic bar stirring.
c. Accurately weigh 16.5 mg Ascorbic acid and 16.5 mg Citric acid.
d. Add the weighed ascorbic acid and citric acid into Tween® 80-Cremophor® EL mixture from "step b" with vigorous magnetic bar stirring.
e. Sonicate for at least 10 minutes to disperse and dissolve organic acids.
f. Continue stirring-sonication cycle until all acids dissolve. It may take around 1-2 hours.
g. Accurately weigh 138 mg docetaxel trihydrate.
h. Divide into several small portions (~30-40 mg each) and add into Tween® 80-Cremophor® EL-ascorbic acid-citric acid mixture from "step f" with vigorous magnetic bar stirring at 35 degrees Celsius.
i. Sonicate for at least 10 minutes to disperse and dissolve docetaxel.
j. Continue stirring-sonication cycle until all docetaxel dissolves. This may take around 4 hours.

5. Measurement of Micelle Sizes for Docetaxel Single and Two-Surfactant Pharmaceutical Compositions in Water.

Single surfactants and two-surfactant docetaxel formulations were diluted to a concentration of 1.25 mg/ml (150 mg docetaxel in 120 ml water) to simulate the dilution conditions in a human stomach. Table 5.1 shows the particle sizes (nm) measured using a Delsa™ Nano C Particle Analyzer (Beckman Coulter, US). Except for Labrasol® compositions, which demonstrated precipitation, all formulations remained in their micellar state under expected dilution conditions in the human stomach.

TABLE 5.1.

| Formulation | Particle size (nm) |
|---|---|
| 100% Tween80 | 17.9 |
| 100% Cremophor EL | 118 |
| 100% Labrasol | Suspension forms |
| 100% Tween20 | 13.4 |
| 80% Tween80/ 20% Cremophor EL | 14.2 |
| 65% Tween80/ 35% Cremophor EL | 13.9 |
| 20% Labrasol/ 80% Cremophor EL | 14.4 |
| 20% Tween20/ 80% Cremophor EL | 14.6 |
| 20% Solutol H515/80% Cremophor EL | 18 |

6. Accelerated Stability of Liquid Formulations with Ascorbic Acid and/or Citric Acid.

Docetaxel liquid docetaxel formulations at concentration 45 mg/ml with the following surfactant ratios were filled into hard gelatin capsules and were subjected to "accelerated stability" conditions (40° C./75% relative humidity):

Example 1: 64.35% Tween® 80, 34.65% Cremophor® EL, 0.5% Ascorbic Acid, 0.5% Citric Acid Example 2: 64.35% Tween® 80, 34.65% Cremophor® EL, 1% Citric Acid Table 6.1 details the composition of each of the formulations.

TABLE 6.1.

| Ingredients | Example 1 | Example 2 |
|---|---|---|
| | Weights (mg) | |
| Docetaxel Trihydrate | 138 | 138 |
| Tween® 80 | 1950 | 1950 |
| Cremophor® EL | 1050 | 1050 |
| Ascorbic acid | 16.5 | 0 |
| Citric acid | 16.5 | 33 |
| Total | 3171 | 3171 |

HPLC analysis of docetaxel in liquid formulation for degradation products.

Dilution of Liquid Formulation (Methanol=1:30)

Docetaxel System Suitability Mixture (USP, Lot no. F0K229) at 1 mg/ml with methanol.

A liquid formulation standard was used to identify the peaks due to the presence of surfactants.

Analytical Conditions:

Instrument: Agilent 1260 Infinity

Chromatographic parameters:

Column: Zorbax Eclipse Plus C18, 4.6*150 mm, 5 μm

Mobile phase: Ultrapure water (A); Acetonitrile (B) (see Table 6.2)

Flow rate: 1.2 mL/min

Column temperature: 45° Celsius

Injection volume: 20 μl

Detection wavelength: 230 nm

Other Conditions Follow the USP35 Docetaxel Injection:

Assays for docetaxel and its degradation products were conducted at initial, 1, 3 and 6 months. Tables 6.3 and 6.4 show that impurity levels for all the liquid formulations containing the various ratios of ascorbic acid and citric acid remained below the USP limits for 6 months at 40° C. and 75% relative humidity. These results indicate that the liquid formulations are stable for the duration of the storage as the levels of all the impurities were below the USP acceptance criteria.

TABLE 6.2.

| Time (min) | Solution A (%) | Solution B (%) |
|---|---|---|
| 0 | 72 | 28 |
| 9.0 | 72 | 28 |
| 39.0 | 28 | 72 |
| 39.1 | 0 | 100 |
| 49.0 | 0 | 100 |
| 49.1 | 72 | 28 |
| 60 | 72 | 28 |

TABLE 6.3

Formulation with 0.5% citric acid/0.5% ascorbic acid.

| Impurities | RRT | Limit (NMT) | Initial | Month 1 | Month 3 | Month 6 |
|---|---|---|---|---|---|---|
| Unknown 1 | 0.68 | N/A | 0 | 0.03 | 0.17 | 0.47 |
| Crotonaldehyde analog | 1.05 | 1.3 | 0 | 0.31 | 1 | 1.2 |
| 6-oxoDocetaxel | 1.08 | 1.5 | 0 | 0.35 | 0.25 | 0.15 |
| 4-epidocetaxel | 1.13 | 0.5 | 0 | 0.06 | 0.15 | 0.38 |
| 4-epi-6-oxodocetaxel | 1.18 | 0.5 | 0 | 0.03 | 0.06 | 0.1 |
| Total Impurities | — | 3.5 | 0 | 0.78 | 1.63 | 2.3 |

TABLE 6.4

Formulation with 1% citric acid.

| Impurities | RRT | Limit (NMT) | Initial | Month 1 | Month 3 | Month 6 |
|---|---|---|---|---|---|---|
| Unknown 1 | 0.68 | N/A | 0 | 0 | 0 | 0.22 |
| Crotonaldehyde analog | 1.05 | 1.3 | 0 | 0.12 | 0.35 | 0.59 |
| 6-oxoDocetaxel | 1.08 | 1.5 | 0 | 0.24 | 0.37 | 0.16 |
| 4-epidocetaxel | 1.13 | 0.5 | 0 | 0.05 | 0.1 | 0.22 |
| 4-epi-6-oxodocetaxel | 1.18 | 0.5 | 0 | 0.05 | 0.08 | 0.07 |
| Unknown 1 | 0.68 | N/A | 0 | 0 | 0 | 0.22 |
| Total Impurities | — | 3.5 | 0 | 0.46 | 0.9 | 1.26 |

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating cancer, comprising orally administering a pharmaceutical composition to an individual in need of treatment for cancer, wherein the pharmaceutical composition comprises a taxane solution consisting of the taxane and a surfactant mixture consisting of a first surfactant that is polysorbate 80 and a second surfactant that is propane-1,2,3-triol-oxirane, wherein the ratio of the first surfactant to the second surfactant in the pharmaceutical composition is from 65:35 to 80:20 by weight, wherein the first surfactant and the second surfactant comprise at least 90% of the pharmaceutical composition by weight, and wherein the pharmaceutical composition is effective to form a micellar suspension.

2. The method of claim 1, further comprising administering a P-glycoprotein inhibitor to the individual in need of treatment for cancer concurrent with or prior to administration of the pharmaceutical composition.

3. The method of claim 2, wherein the P-glycoprotein inhibitor is HM30181.

4. The method of claim 1, wherein the taxane is selected from the group consisting of paclitaxel, docetaxel, cabazitaxel, larotaxel, ortataxel, and tesetaxel.

5. The method of claim 1, wherein the pharmaceutical composition further comprises a stabilizer.

6. The method of claim 5, wherein the stabilizer comprises at least one of citric acid and ascorbic acid.

7. A method of increasing at least one of taxane oral bioavailability, peak plasma concentration, and area under the curve for a taxane in an orally administered pharmaceutical composition comprising a taxane solution, wherein the taxane solution consists of the taxane in combination with a surfactant mixture consisting of a first surfactant that is polysorbate 80 and a second surfactant that is propane-1,2,3-triol-oxirane, wherein the ratio of the first surfactant to the second surfactant in the pharmaceutical composition is from 65:35 to 80:20 by weight, wherein the first surfactant and the second surfactant comprise at least 90% of the pharmaceutical composition by weight, and wherein the pharmaceutical composition is effective to form a micellar suspension.

8. The method of claim 7, wherein the taxane is selected from the group consisting of paclitaxel, docetaxel, cabazitaxel, larotaxel, ortataxel, and tesetaxel.

9. The method of claim 7, wherein the pharmaceutical composition further comprises a stabilizer.

10. The method of claim 9 wherein the stabilizer comprises at least one of citric acid and ascorbic acid.

11. A method of treating cancer, comprising orally administering a pharmaceutical composition to an individual in need of treatment for cancer, wherein the pharmaceutical composition comprises a taxane solution consisting of the taxane and a surfactant mixture consisting of a first surfactant that is polysorbate 80 and a second surfactant that is polysorbate 20, wherein the ratio of the first surfactant to the second surfactant in the pharmaceutical composition is 65:35 by weight, wherein the first surfactant and the second surfactant comprise at least 90% of the pharmaceutical composition by weight, and wherein the pharmaceutical composition is effective to form a micellar suspension, and further comprising administering a P-glycoprotein inhibitor to the individual in need of treatment.

12. The method of claim 11, wherein the P-glycoprotein inhibitor is HM30181.

13. The method of claim 11, wherein the taxane is selected from the group consisting of paclitaxel, docetaxel, cabazitaxel, larotaxel, ortataxel, and tesetaxel.

14. A method of increasing at least one of taxane oral bioavailability, peak plasma concentration, and area under the curve for a taxane in an orally administered pharmaceutical composition comprising a taxane solution, wherein the taxane solution consists of the taxane in combination with a surfactant mixture consisting of a first surfactant that is polysorbate 80 and a second surfactant that is polysorbate 20, wherein the ratio of the first surfactant to the second surfactant in the pharmaceutical composition is 65:35 by weight, wherein the first surfactant and the second surfactant comprise at least 90% of the pharmaceutical composition by weight, and wherein the pharmaceutical composition is effective to form a micellar suspension, and further comprising administering a P-glycoprotein inhibitor.

15. The method of claim 14, wherein the taxane is selected from the group consisting of paclitaxel, docetaxel, cabazitaxel, larotaxel, ortataxel, and tesetaxel.

* * * * *